United States Patent
Korenman et al.

[19]

[11] Patent Number: 6,026,322
[45] Date of Patent: Feb. 15, 2000

[54] BIOFEEDBACK APPARATUS FOR USE IN THERAPY

[75] Inventors: Ernesto Marcelo Dario Korenman, Wembley; Tuvi Orbach, London; Bernard William Watson, Harpenden, all of United Kingdom

[73] Assignee: Ultramind International Limited, Jerusalem, Israel

[21] Appl. No.: 08/796,811

[22] Filed: Feb. 6, 1997

Related U.S. Application Data

[62] Continuation-in-part of application No. 08/190,163, Feb. 7, 1994, abandoned, and application No. 08/754,102, filed as application No. PCT/GB92/01477, Aug. 7, 1992.

[30] Foreign Application Priority Data

Aug. 7, 1991 [GB] United Kingdom .................... 9117015

[51] Int. Cl.$^7$ ........................................................ A61B 5/00

[52] U.S. Cl. ............................................................ 600/547

[58] Field of Search ................................... 600/547, 546, 600/557, 558

[56] References Cited

U.S. PATENT DOCUMENTS

| | | | |
|---|---|---|---|
| 4,632,126 | 12/1986 | Aguilar | 128/732 |
| 4,683,891 | 8/1987 | Cornellier et al. | 128/630 |
| 4,800,893 | 1/1989 | Ross et al. | 128/732 |
| 5,343,871 | 9/1994 | Bittman et al. | 128/732 |

*Primary Examiner*—Max Hindenburg
*Attorney, Agent, or Firm*—Breiner & Breiner

[57] ABSTRACT

Apparatus and a program designed to train the user to control one or more aspects of his or her psycho-physiological state is controlled by signals representative of a psycho-physiological parameter of the user, e.g. galvanic skin resistance. This may be detected by a sensor unit with two contacts on adjacent fingers of a user. The sensor unit can be separate from a receiver unit which is connected to a computer running the program. The apparatus is described for use in treating patients with a physiological condition, for example, irritable bowel syndrome. In a treatment session, one or more psycho-physiological parameters of the patient is sensed and the sensed parameter used to alter a display which the patient watches. The display includes a visual or pictorial representation of the physiological condition being treated which changes in appearance in a fashion corresponding to the physiological change desired in the patient.

11 Claims, 5 Drawing Sheets

BIOFEEDBACK APPARATUS FOR USE IN THERAPY

RELATED APPLICATIONS

The present application is a continuation-in-part application of Ser. No. 08/190,163 filed Feb. 7, 1994, now abandoned and and is a CIP of Ser. No. 08/754,102, filed on Nov. 20, 1996. This application is based on PCT/GB92/01477 filed Aug. 7, 1992.

FIELD OF THE INVENTION

This invention relates to the operation of computer systems in therapy using biofeedback techniques.

BACKGROUND OF THE INVENTION

In recent years, the development of the so-called "personal computers" has enabled computing power to be made available to millions of people. In parallel with the development of the hardware, there has been major growth in the amount of software being written. In a computer system, the user operates the computer by first controlling it with the aid of software to be ready to operate in accordance with a desired program, and then inputting data and producing output data from the computer.

In order to input data, a variety of devices may be used, the most common of which is a keyboard. The most common output device is a visual display unit (VDU) or screen on which the results of operations within the computer may be displayed to be read (if expressed in words) and/or viewed by the user.

Other input may be fed into the commuter in known fashion. For example, most computers have one or more communications ports which can send or receive data in the form of digital signals. The data can be received, e.g., from sensor units via appropriate interface circuits, or from other computers. It is known that a very wide variety of sensors may be used, including sensors which sense human physiological parameters, for example blood pressure or electrical currents in the body (in computer-controlled electrocardiogram or electroencephalogram systems). However, up until now such uses have been mainly confined to those where the computer user has not been the same person as the person under test.

An example where such use is not confined to those where the computer user has not been the same person is shown in published International Application WO 86/01317 which discloses using galvanic skin resistance to input data into a computer, and deals: specifically with the electronics necessary to overcome the problem of the very wide range of galvanic skin resistances that may be sensed over a period of time and from one user to another.

Published International Application WO 89/02247 discloses a system whereby a computer user may monitor his or her heart activity using; a simple probe which connects to the input of the computer. A suitable program must be loaded into the computer in order to enable display or printout representative of the user's cardiac function to be effected. Published European Patent Application 0176220 also discloses using a computer to monitor a user's heart.

Published International Application WO 91/01699 discloses use of a computer and suitable sensor means to offer limited mobility and limb movement patients a means of operating a computer. U.S. Pat. No. 4,894,777 uses sensor means to detect when a computer user ceases to concentrate on the subject they should be concentrating on, and published UK Patent Specification 2079992A discloses using a sensor means and microcomputer to predict the fertility period in a woman's menstrual cycle.

In recent years it has become established that physiological conditions may be treated using so-called biofeedback techniques. By measuring an appropriate psycho-physiological parameter, for example an electrodermal activity parameter, heartbeat, brain waves or the like, and displaying that measurement to the subject undergoing treatment or, therapy, it becomes possible for the subject, when appropriately trained and motivated, to control his or her psychological and/or physiological functioning or condition so as to influence the parameter being displayed. Substantial success has been reported in a variety of areas, but success is somewhat unpredictable and some patients find the techniques difficult to follow or practice or the apparatus used forbidding- All this does not assist satisfactory therapy.

For example, biofeedback apparatus is described in U.S. Pat. Nos. 4,800,893; 4,632,126; 5,253,168 and 4,354,505; British Application No 2186375A; and published International Application WO 95/02989. These apparatus each describe relating some animated image to a monitored physical condition of a user. However, it has been reported previously that psychotherapeutic treatments are often more effective in terms of improving physiological conditions if the patient undergoing treatment is taught how to visualise in a very pictorial way the physiology or anatomy of the condition in question. This can promote a better understanding of the condition and enhance the treatment process, especially in the case of physiological conditions that are known to be influenced by psychological factors Biofeedback treatment presents information about the patient's physiological and psycho-physiological state to the patient in a form that can be understood by the patient's logical and cognitive faculty (graphs, numeric displays, etc.). This type of treatment is appropriate to certain types of patient, notably those who have the capacity to grasp such cognitive/logical information.

Visualisation treatment, in contrast, works the opposite way in that it is directed at the patient's emotional faculty. In many cases it is used in conjunction with therapeutic hypnosis. Moreover, the visualisation is done when the patient closes his eyes and visualises internally through imagination, either with or without hypnosis. For example in the treatment of Irritable Bowel Syndrome (IBS), the hypnotherapist would encourage the patient to relax and to visualise his digestive system working in a better rhythm and the pain disappearing. But only a minority of people can be hypnotised or can visualise through imagination alone.

Nowhere in the prior art has any attempt been made to combine these radically differing methods of treatment into a single system wherein biofeedback is combined with visualisation.

Similarly, desensitisation treatments of psychological conditions, such as post-traumatic stress disorder (PTSD) and phobias, work by showing the user real or simulated visual/pictorial representations of the cause of the condition such as the traumatic event or the cause of the phobia with progressively increasing duration and intensity (i.e. more traumatic or frightening) so as to progressively render the patient less anxious in the face of such negative stimuli. For example, a PTSD patient who was involved in a car accident might be shown pictures of a wrecked car and sounds of police sirens, followed by pictures of the victim and later an animation and sound of a car accident taking place.

However, such methods of desensitisation treatment impose upon the therapist the burden of assessing when the patient has made sufficient progress to move on to the next stage of the treatment process in terms of duration and intensity of the images. Moreover, such methods require the presence of a therapist to regulate the progress of the treatment because a self-treatment desensitisation program would expose the patient to the risk of being prematurely exposed to a negative stimulus before they are psychologically ready to cope with it.

GENERAL DESCRIPTION OF THE INVENTION

According to the present invention, there is provided computer-based biofeedback apparatus including means for sensing one or more psycho-physiological parameters of the patient, and means for altering a display visible to the patient following changes in the parameter(s), and which is characterised in that the display includes visual or pictorial representations of the physiological or psychological condition being treated or the cause of such condition which change in appearance following a change in the parameter sensed in a way corresponding to the physiological or psychological change desired in the patient.

Using modern computer graphics and particularly computer animation techniques, supplemented by appropriate programming, it is possible to put the present invention into practice with relatively low outlay. For example, the apparatus for testing an aspect of one or more users' psycho-physiological condition which provides an image display, in particular any visual image such as words or pictorial representations, which is viewable by the user and which at least provides images related to or concerning the user's substantially current psycho-physiological condition reflected by that aspect being tested, and which may provide one or more stimuli to the user, comprises a computer system, an input device, and software capable of interpreting data input from the input device and displaying the required image. The input device is adapted to be attached to one or more users and periodically to sense at least one psycho-physiological condition and to transmit data corresponding to the user's psycho-physiological condition to the receiver unit. The input device is further adapted to input the data concerning the user's condition into the computer system. The input device can consist of a sensor unit and a receiver unit that are separate from each other, e.g. communicating by wireless means rather than simply connected together by a cable.

Such apparatus, providing the program or software is appropriate, can also be used to enable control of the computer images by way of the user's control of one or more of his or her psycho-physiological parameters. Thus, the precise running of programs can depend on both conscious input from the user and on one or more psycho-physiological parameters of the user.

In using the apparatus, the user can interact with the programmed computer via two channels, the conscious voluntary channel, e.g. mediated via a standard keyboard or via keys on a keypad forming part of the sensor unit and an unconscious involuntary channel, e.g. mediated via a galvanic skin resistance (GSR) sensor and appropriate circuitry to feed a signal representative of GSR to the receiver and thence the computer system. It is known that GSR correlates with arousal/relaxation. Thus, the operation of the computer system may be mediated not merely by the user's keyboard input but by his or her state of arousal. The programming of the computer system is of a type designed to teach definite behavioural skills in order to affect and thus control the state of a physiological condition.

The novel feature of this invention is that it adds two additional aspects to biofeedback. The first is that the patient visualises the improvement in his condition not in his imagination but on a screen. Therefore, even people who find it hard to visualise mentally can see these images and results on the screen. Consequently, the method is applicable to all types of patient (except the blind). The second aspect is that the visualisation on the screen is driven specifically by the physiology of the patient's body as measured by the sensors. Thus the patient can see a direct correlation between his internal actions and intentions on the one hand and the image of the relevant part of the body (as simulated in the graphical display) on the other.

The method is much more effective for two reasons. Firstly, the patient can learn to control the relevant aspect of physiology because he is getting feedback to show when he is doing things correctly (relaxing, breathing properly, etc.). This constitutes learning through trial and error. Secondly, the patient gets positive feedback, reinforcement and assurance which gives him more confidence and enhances his self-belief when he is making progress. A lot of research has shown that when a person gets assurance and positive reinforcement, it enhances the therapeutic and curative effect of the treatment. (This effect is seen in medical trials when a patient's condition improves when he or she is given a placebo, but combining visualisation with biofeedback enhances this effect).

An example of how the present invention may be put into practice is now described., In this example, the target condition which it is desired to alleviate is the so-called irritable bowel syndrome. The exact causes of this syndrome are not fully known, but many cases are aggravated by stress-related factors. Stress affects the digestive tract via various neurohormonal paths, but the details are not completely understood. The manifestations of irritable bowel syndrome are abdominal discomfort or pain, irregular stool conditions and bloating. The pathogenesis is multifactoral and appears to reflect in interplay of psychological and physiological responses. Relaxation techniques can assist in moderating those responses and allowing the digestive tract and particularly the bowels to function in a normal manner.

Relaxation is commonly correlated with electrodermal activity parameters, particularly of a person, and this thus provides a simple means of monitoring relaxation. A pair of electrodes is attached at two spaced apart locations to a person, for example to the palmar surfaces of two adjacent fingers on the same hand, and suitable associated circuitry is connected thereto to enable the electrodermal activity to be measured. The measurement may be reflected in a suitable parameter of a signal sent to a programmed computer which has a display viewable by the patient/user.

Use may be made of the circuitry techniques described below.

The electrodermal activity signal constitutes a varying input to the computer programmed to respond to changes in that input. A typical program will operate under the control both of that parameter, but more importantly also under the control of the program user. For example, the program on loading may cause the screen to display a menu giving a variety of options selectable in customary fashion using a mouse, keyboard, keypad or the like. Appropriate options are informational material, text and/or graphics, concerning irritable bowel syndrome, an explanation of the treatment part of the program and a menu option to select actual treatment.

The treatment part of the program may consist, for example, of screens prompting the user to identify the type, position and/or severity of the pain they are currently experiencing. Following that, the program may provide by way of animated screen a pictorial view as would be seen by a notional traveller through the stomach and down the digestive tract, i.e. a pictorial image of the physiological condition being treated. When the traveller approaches the identified pain site, the pictorial or graphic representation may be altered in colour or fill-pattern such as to indicate, e.g., the accumulation of air bubbles (when the patient suffers from bloating) or a constriction (where the patient suffers bowel spasm).

At this point, the screen display is preferably controlled effectively by the degree of relaxation exhibited by the patient/user, i.e. it varies depending on the psycho-physiological parameter of the user being sensed, for example electrodermal activity. As the patient becomes more relaxed, the program controlling the computer system may cause the appearance of the pictorial image to change. For example, a set of displayed bubbles may start to be reduced in size or disappear altogether, while if the patient becomes less relaxed, the pictorial representation of a bubble blockage may appear firmer or more solid on the screen. By concentrating on the screen, and relaxing, the patient may gradually cause the bubbles to appear to vanish or dissolve. The program which controls the graphic display on the screen may then arrange to modify the display to give the user the impression of moving further down the digestive tract and past the site of the (now cleared) bubble blockage.

An alternative visualisation, where the pain is envisaged as internal inflammation, is to colour the walls of the digestive tract at the pain site red, and gradually changing it to pink as the patient relaxes (as detected by EDA monitoring), whereafter again the graphic display may appear to let the viewer travel past the site of the (now reduced) inflammation.

It is found that graphic visualisation of a person's physiological problems in this anatomical way leads to substantially enhanced rates of successful treatment.

Likewise, if the target condition to be treated is a cardiovascular disorder, the software may contain a visual representation of the cardiovascular system and may provide an animated view of a notional traveller navigating through the cardiovascular system. The same method would be used of varying the colour, shading, shape or movement of different areas of the image to represent pain, contraction or dilation in a particular area, with the colours, shading, shape and movement returning to a recognisable norm when the user relaxes, said relaxation being indicated by the user's EDA measurements sensed by the sensor device.

Other target conditions such as Raynaud's disease, asthma and other respiratory disorders, insomnia and other sleep disorders, headaches and migraine, depression and anxiety could all have modules appropriately designed for them, using the same general principle of illustrating the affected area of the body and using variation in colour, shading, shape and movement of the image to illustrate pain, discomfort or the absence thereof.

In the case of a tension headache application, for example, the patient can be shown an animated graphic illustration of the network of arterioles in the brain, wherein the arterioles contract when the sensors indicate that the patient is stressed and dilate when the patient is relaxed.

In the case of an anxiety or depression application, the patient could be shown an animated graphic illustration of a person looking anxious or unhappy when the patient is anxious and appear happy and relaxed when the patient's anxiety level falls, as indicated by his or her EDA level.

Similarly, applications designed for desensitisation of patients suffering from phobias or PTSD could show biofeedback information in conjunction with negative stimuli in the form of imagery and sound effects of the object of the phobia or of the traumatic event that caused the PTSD and also in conjunction with positive stimuli in the form of encouraging text, speech and relaxing music. The positive encouragement offered through speech may be audible, so as to register on the conscious mind, or inaudible, so as to be absorbed by the subject at the non-conscious level. As the treatment proceeds and the user's stress response to the negative stimuli becomes less intense, the imagery could be shown with greater clarity, duration and intensity.

The novel feature of this approach is that whereas in conventional desensitisation the therapist has to assess the progress of the patient by external observation so as to decide when to progress the treatment to the next level, in this system the therapist can obtain diagnostic information about the user's internal stress response through measurements taken by the sensors. Furthermore, the measurements from the sensors can also be used to control, directly and automatically, the progress of the session from one level to the next. Thus the patient can see his or her response and to control and improve his or her reaction.

To put the invention into effect, it is necessary to have computer apparatus arranged to provide a visual output under control of a program, the output being dependent on input via the keyboard and/or input via a psycho-physiological parameter sensor located to monitor such a parameter of the user.

In principle, the display viewed by the user may vary widely and consist of graphics, animation, text, speech, video, audio music, sound effects or combinations of these. The timing of image display will be controlled by the program. The program may be one which displays subliminal stimuli via the screen as well as consciously perceptible images. The program may be arranged to display to the user an indication of the psycho-physiological parameter measured, thus enabling the user to try and consciously moderate or modify their response in view thereof. The program may also control audio output devices and, for example, cause a voice or sound synthesis module within the system to generate speech, music and/or other sound, all coordinated with the desired therapeutic treatment to be effected.

The conscious interaction between computer system and user may also be mediated via one or more standard usually manually controlled devices, e.g., keyboard, mouse, joystick. The unconscious interaction via the sensor may rely on one or more parameters, for example, GSR, electrodermal activity, brain or cardiac electrical signals (as in EEG and ECG monitoring), heart or pulse rate, skin temperature, or others.

It is known that in most cases of changes to a single user parameter, the relation between casual factors and the changes to the parameter in question is many-to-one. Thus, a single change in a single physiological parameter may be due to more than one cause- However, if a sufficient number of parameters are measured (such as electrodermal activity, heart rate, EEG, blood pressure, etc.), it is possible to find unique combinations and patterns of changes such that the relationship between causes and discernible patterns is one-to-one. Thus, it is possible, by measuring several user parameters, to isolate subtle differences in the user's physiological responses depending on the precise causes in the user's psychological state or physical circumstances. These differentiated patterns may be detected by neural network software and/or pattern recognition software, such as already exists.

The software may also identify a correlation between a distinctive pattern on the one hand and a particular mental, psychological or emotional state on the other, by the method of taking information input from the user's conscious cognitive faculty in the form of answers to questionnaires about the user's conscious state that may appear on the screen and be answered via the keyboard or by a mouse and pointer.

The association between a distinctive user physiological response pattern and a psychological cause can also be made by the software by other methods, such as those resembling classical conditioning, wherein the software provides a stimulus with a known normal response. For example, the computer may tell a joke or display a humorous image or animation and the software may correlate it to the user's multi-parameter physiological response, thereby identifying a physiological response pattern to a humour type stimulus.

After the software has identified a particular user response pattern and its cause, the system may train the user to invoke or eliminate said response pattern at will, depending on whether it is associated with a negative or positive mental state, by means of the same multimedia biofeedback and visualisation methods as described elsewhere in this specification.

BRIEF DESCRIPTION OF DRAWINGS

Embodiment of apparatus in accordance with the invention will now be described, by way of example, with reference to the accompanying drawings, in which.

DESCRIPTION OF PRESENTLY PREFERRED EMBODIMENTS

Figures 1, 2A:
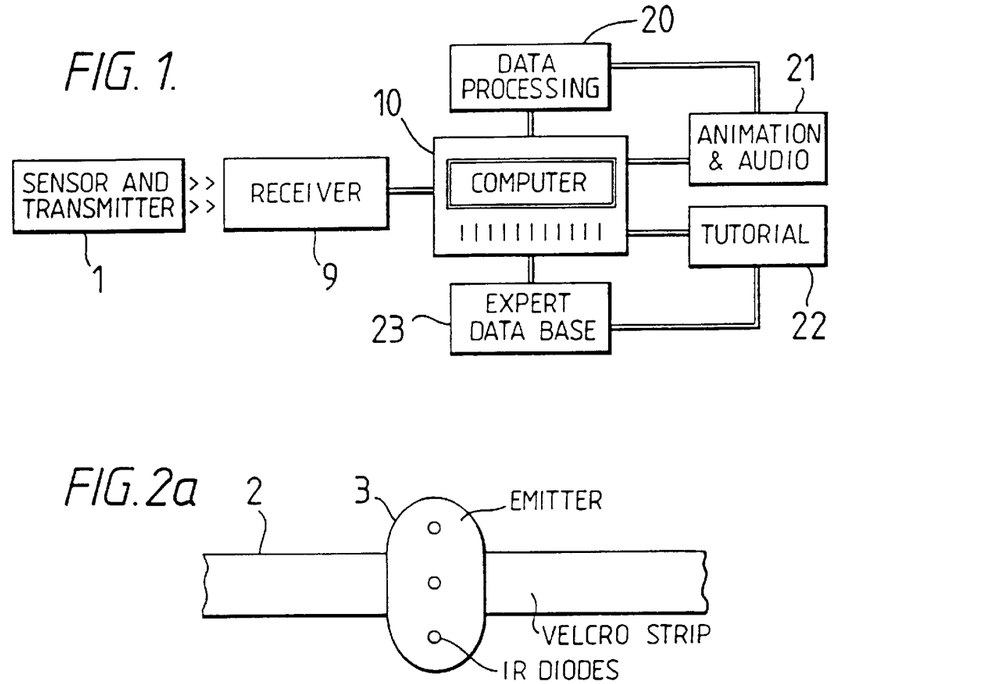
FIG. 1 is a block diagram of apparatus for use in interactive training mediated by psycho-physiological performance.
FIG. 2a and 2b show front and back views of a sensor for attachment to a person's wrist.
Figure 2B:
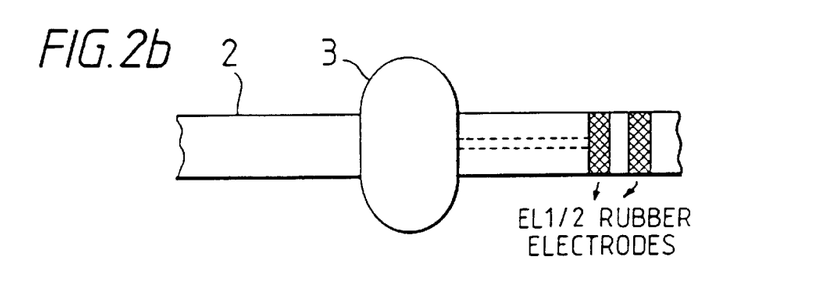
Figure 2C:
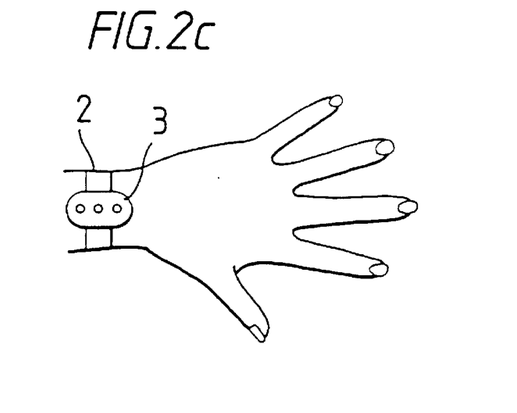
FIGS. 2c and 2d show front and back views of a hand and wrist with the sensor of FIGS. 2a and 2b attached.
Figure 2D:
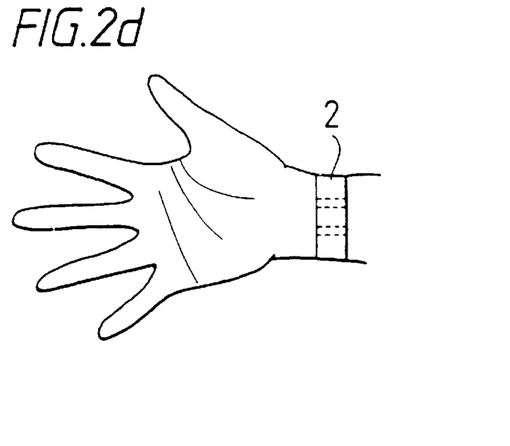

In the apparatus of FIG. 1, signals representative of a parameter being sensed by a sensor are sent via an infrared link from a sensor and transmitter 1 to a receiver 9.

The sensor comprises an attachable wrist-belt 2 (FIGS. 2a to 2d) carrying two pads which abut the skin and a micro-electronic device to detect the galvanic skin resistance (GSR) of the wearer. The device is mounted in a watch-like case 3 and connected electrically to two rubber skin electrodes EL1 and EL2. A stabilised voltage Vref (FIG. 3) is applied in series with resistors R1 and R2 and the two electrodes EL1 and EL2. When the wearer's skin resistance increases, the voltage between the electrodes and the output voltage V0 which feeds the input to a high impedance buffer amplifier 4, both rise. A corresponding signal is emitted by infrared emitter diodes to be received by a receiver 9.

Galvanic skin resistance levels can vary over a range of over 100 to 1. The simple input arrangement illustrated in detail in FIG. 3 offers two special benefits for GSR measurement. First, the output voltage never saturates, even though its response may be low at extreme resistance values; and second, over a useful resistance range of about 30 to 1, the output voltage responds approximately linearly to the logarithm of skin resistance. These features provide an orderly and stable compression of the large input parameter range, allowing satisfactory transmission within the rather restricted, typically 4 to 1, modulation range of the simple telemetry system used. Resistor R2 limits the minimum output voltage from the chain. Thus, an input circuit for providing a linear output corresponding substantially to the logarithm of GSR is provided.

Figure 3:
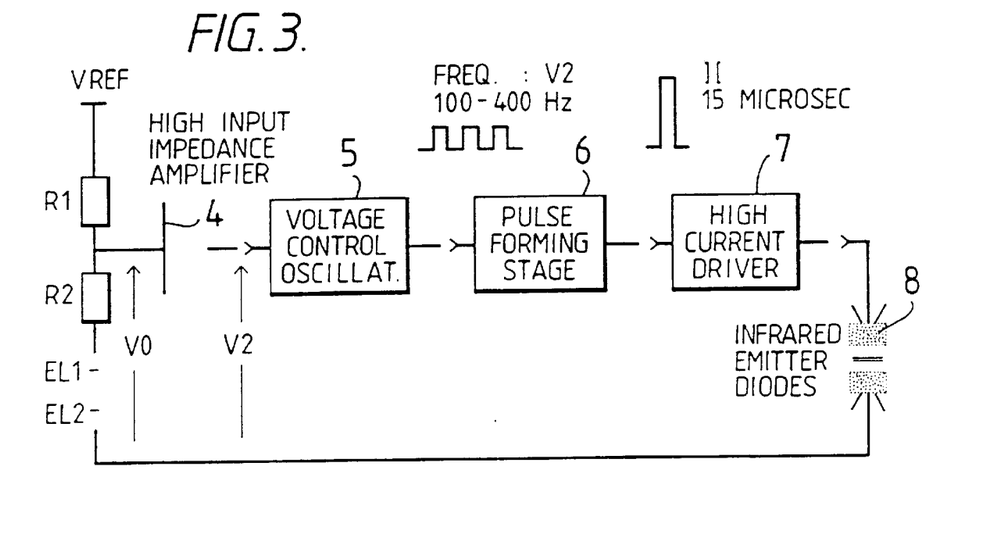
FIG. 3 is a block diagram of an infrared biotelemetry transmitter.

The output voltage V2 from the buffer amplifier feeds the input of the following voltage controlled oscillator 5 section which generates a square wave output of frequency proportional to V2. The oscillator 5 output frequency can vary from about 100 to 400 Hz corresponding to input extremes of zero and infinite resistance at the electrodes but generally lies within the 150 to 350 Hz range in normal operation.

The square wave output from the oscillator 5 is fed to the pulse forming stage 6 which generates a rectangular pulse of about 15 microseconds duration following every negative going transition of the oscillator 5 output form. This output pulse turns on a transistor driver stage 7 which delivers a 15 microsecond 0.6 Å current pulse to infrared emitting diodes 8.

The transmitter 's powered by a PP3 9 V dry battery of about 400 mAH capacity allowing for at least 60 hours of operation before battery replacement.

Figure 4:
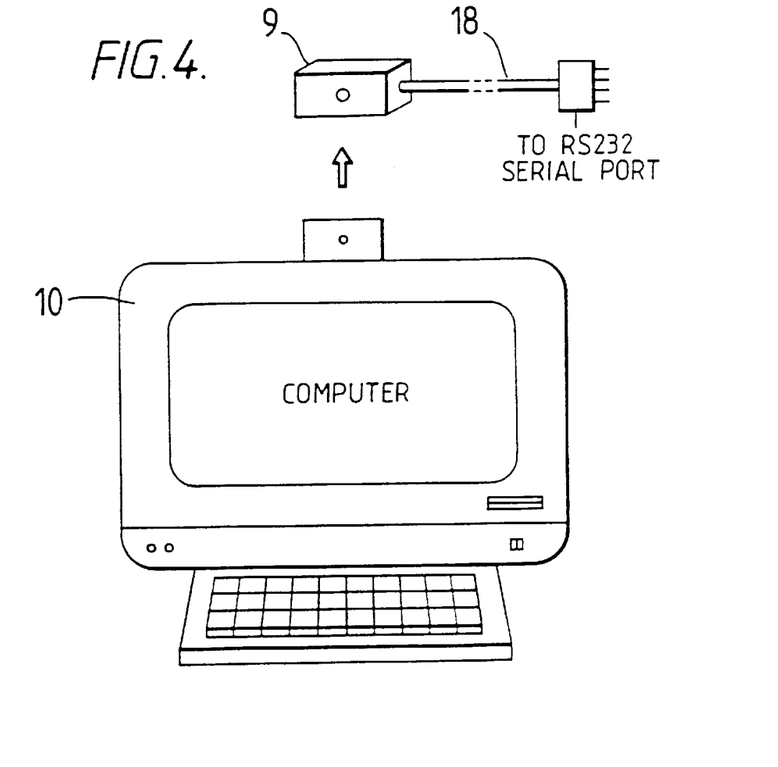
FIG. 4 is a diagram of portions of the apparatus of FIG. 1.

The receiver 9 is mounted in a small plastic box to be placed on top of a computer screen 10 (FIG. 4). Pulses of infrared radiation emitted by the transmitter 1 are detected by a reverse biased large area PIN photo diode 11 (FIG. 5) with integral infrared filter.

Figure 5:
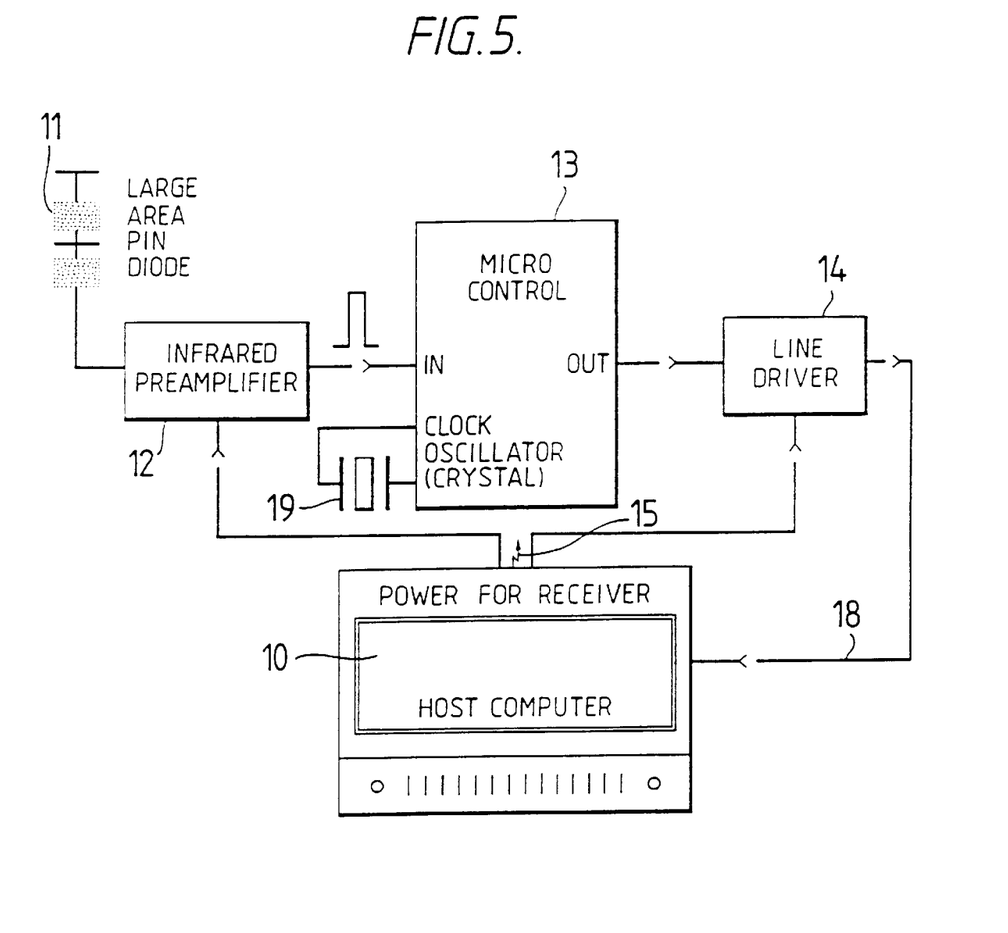
FIG. 5 is a diagram of an infrared telemetry receiver.

Photocurrent from diode 11 is fed to the input of an infrared pre-amplifier integrated circuit 12. The passband of this pre-amplifier is designed to reject the effects of unwanted infrared radiation, e.g. from sunlight, lighting fixtures and other interfering sources. A rectangular pulse of about 25 microseconds duration is generated at the pre-amplifier output following the reception of each pulse from the transmitter.

The pre-amplifier output pulses are fed to the input of a one-chip micro-controller 13 which counts the incoming pulses over a sampling period of about 95 milliseconds and then computes the corresponding pulse frequency to 12-bit precision. This value is then incorporated into two data bytes which are serially output from the micro-controller at a data rate of 9600 bits per second. Additional bits identify the most significant byte and flag the received signal quality.

A transistor line driver 14 then delivers this signal at the appropriate voltage levels through a receiver output cable 18 to a serial port RS232 of the host computer 10. Output sample rate is 10 per second. Output values sent from the receiver retain the quasi-logarithmic relation to the subject skin resistance. This can be expanded by the host computer if desired.

The micro-controller 13 operating program incorporates several measures to maintain very low noise levels and good output recovery characteristics in spite of the effects of interference and subject movement.

These include the rejection of pulses arriving at irregular intervals and the handling of periods of signal loss which occurs particularly when the pre-amplifier automatic gain control sub-system cannot adapt fast enough to sudden reductions in received pulse intensity following subject movement. Poor reception quality as determined by received pulse regularity and other criteria applied within the microcontroller program is signalled by an auxiliary bit within the information sent to the host computer 10 as determined by a clock oscillator 19.

The modest power requirements of the receiver are obtained from the host computer's communication port 15, eliminating the need for a separate receiver power supply.

The data is received as a standard RS232 input and for data processing 20 (FIG. 1) is specially encoded. Meanwhile, possible errors are detected and corrected. Then data is decoded and separated into status and parametric data. The parametric data is fed as an input to the analysing systems, which coordinate with animation, audio and other specialised systems determined by the program being run in the computer.

The analysing system stores the data, which can be used to create various types of graphs and charts. These can be used to profile, compare or monitor the subject's accomplishment on-line or during subsequent analysis sessions.

Software for the computer can provide for a variety of psychological testing systems. For example, in an animation system 21 (FIG. 1), data is used to manipulate various segments of the computer screen. Changes in input data produce changes in the speed and path of animation. The procession of images encourages the user to continue adding to the metamorphic in a logical and aesthetic way.

Figure 6:
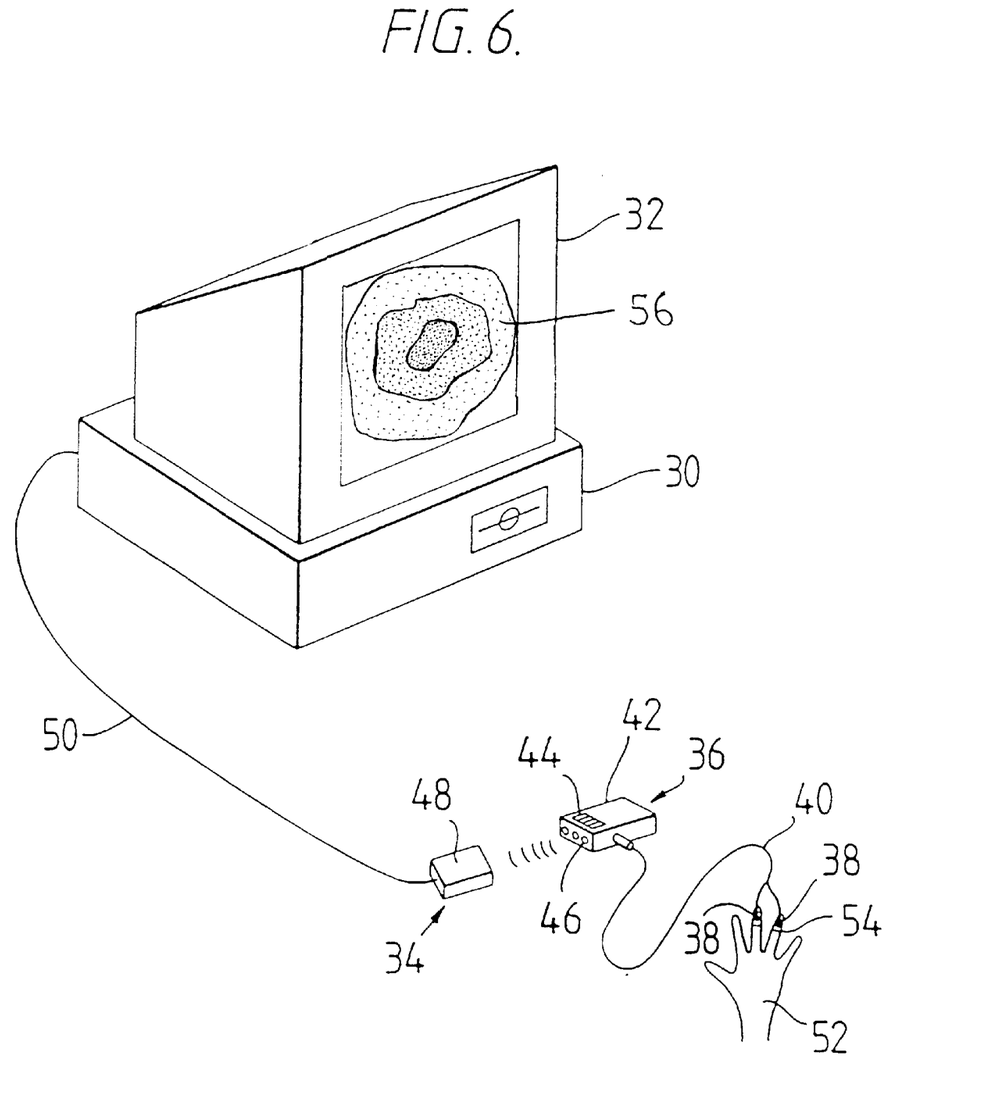
FIG. 6 is a schematic view of a particularly preferred embodiment of the present invention.
Figure 7:
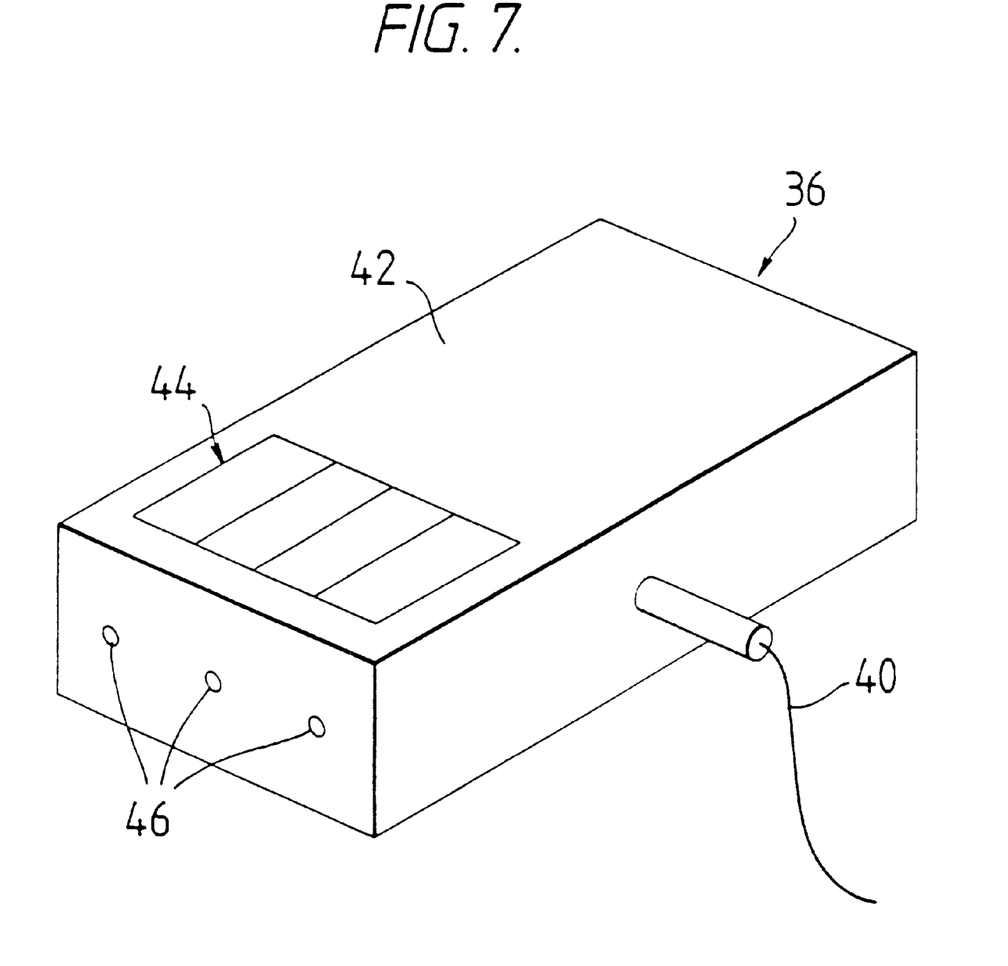
FIG. 7 is an enlarged view of a portion of FIG. 6.

The animation system allows for different levels of advancement. This ensures the adaptation of the system to the particular variations of the user. Therefore achievement, i.e. evolution of images, is always possible. In an audio system 21 (FIG. 1), there can be an option to have an audio response which includes both music and voice. This will also be integrated with the psycho-physiological input FIGS. 6 and 7 show a particularly preferred embodiment of the present invention, comprising a computer 30, a monitor 32, a receiver 34 and a sensor unit 36.

Sensor unit 36 comprises a pair of non-invasive skin contact electrodes 38 connected by wires and a jack plug 40 to a sensor box 42. Sensor box 42 contains appropriate electronics (not shown) to convert the resistance between the electrodes 38 into a digital format signal. Sensor box 42 also contains switches 44 and infrared transmitters 46.

Receiving unit 34 comprises receiver box 48 and a wire and connector 50. This connector 50 connecting into a data entry port (not shown) on computer 30. This may be a standard serial communications part. Receiver box 48 contains an infrared receiver (not shown) and electronics appropriate to convert received infrared signals into computer usable form.

In use, electrodes 38 are applied to adjacent fingers of a user's hand 52 and held in position by way of a band surrounding both electrode and finger 54. The band is preferably secured in place by burr fastener material (e.g. VELCRO), but other suitable systems may be used. The electronics in sensor box 42, powered by a power source also contained in sensor box 42 (not shown) periodically assess the skin resistance of the user via electrodes 38. The electronics in sensor box 42 convert the readings of galvanic skin resistance into a data form suitable for transmission, and send the suitable data form to the infrared transmitters 46 for transmission.

The infrared receiver in receiver box 48 receives the transmissions from infrared transmitters 46 and directs them to the electronics in receiver box 48. There the data is converted into a form suitable for inputting into the computer 30 which is running under the control of an appropriate computer program. In the particular example embodiment described above as to irritable bowel syndrome, the software running on computer 30 in the treatment portion of the program is generating on monitor 32 an image of the interior of a bowel 56 which is provided so as to mirror the physiological condition being treated. For example, if inflammation of the bowel is the symotom being treated, the user can first be shown the bowel as present in the body with the area to be treated highlighted. Thereafter, the interior of the bowel is shown. The images shown are based on actual interior bowel structure as viewed by a camera passing through a bowel. Thus, the animation image is based on the physiological condition being treated. With inflammation of the bowel, the animated image corresponds to the view of the interior of the bowel. The bowel will be a healthy coloir as the animation begins and when the inflamed area is reached, as the viewer seems to progress through the bowel, appropriate changes in the animation occur, i.e. the colour will be shades of red and pink depending on the level of irritation and swelling may be present if this is a symptom also being treated. As the user becomes more relaxed, the user's galvanic skin resistance will rise. This will be detected by electrodes 38 and conveyed to the computer via sensor unit 36 and receiver unit 34. The software will generate graphics showing the inflammation being relieved, i.e. going from red to lesser degrees of red, to shades of pink and finally to a healthy pink colour as well as decrease in swelling if present. As the physiological condition is relieved, the software is arranged to change the display. Such change in display occurs substantially concurrently with the change in the psycho-physiological parameter being monitored, i.e. in real time, so that the patient/user immediately benefits, i.e. can see the effect and learn to effectively comnensate as desired. If, during this process, the user becomes less relaxed and thus causes his/her galvanic skin resistance to drop, the image reverts back to the preceding condition based on the change in the user. The relative image, therefore, allows the user to ascertain his or her progress. Based on repeated use or training, a user can learn how to treat or modify the physiological condition when it occurs in an every day setting.

The software runnig on computer 30 may do more than simply show pictures. Switches 44 on sensor box 42 may be used to exert overall control over the software. For example, buttons 44 might represent an escape button to move the user out of a particular aspect of a program and into a menu, a pair of direction buttons to move around that menu once entered and an enter button to miake selections from the menu. Such buttons enable the use of a customary keyboard forming part of the computer system to be dispensed with. Thus, if the user is not progressing satisfactorily, a tutorial or other explanatory image may be accessed to assist the user in achieving the desired goal, i.e. control of a particular physiological condition. Further, audio means may be part of the computer system. The audio means will provide tones that vary, i.e. in frequency and/or pitch, based on changes sensed in the patient/user. The audio can be designed to assist in relaxation of the user and/or otherwise designed to promote the learning process.

It will be obvious that the software running on computer 30 may have to take into account many different aspects relating to training, testing and assessment of the user.

Psycho-behavioural and Psychometric Test software may be incorporated in the program in the computer system to provide a computerised testing facility which uses conventional methods of administration and interpretation. This may provide a method of detecting psycho-behavioural blockage-points during use of the system.

As will be apparent to one skilled in the art, various modifications can be made within the scope of the aforesaid description. Such modifications being within the ability of one skilled in the art form a part of the present invention and are embraced by the appended

We claim:

1. Biofeedback apparatus comprising a computer system having an image display means viewable by a user of the apparatus, said computer system being programmed to provide on said image display means visual or pictorial representations of a body subject which gradually change in appearance depending on a physiological or psychological condition, a user input means comprising a sensor unit and a receiver unit, said sensor unit structured for attachment to a user, for sensing at least one psycho-physiological parameter of the user, and transmitting data sensed by the sensor unit to the receiver unit, said receiver unit structured to input the data received to the computer system; and means for changing said visual or pictorial representations based on changes in said data sensed substantially concurrently with the changes in the data sensed so that gradual change in the visual or pictorial representations corresponds to gradual change in the at least one psycho-physiological parameter of the user.

2. Biofeedback apparatus according to claim 1 wherein the visual or pictorial representations are a computer graphics animated display.

3. Biofeedback apparatus according to claim 1 wherein the sensor unit comprises a means for sensing electrodermal activity of the user.

4. Biofeedback apparatus according to claim 2 wherein the sensor unit comprises a means for sensing electrodermal activity of the user.

5. Biofeedback apparatus according to claim 1 wherein the computer system further comprises audio means which provide audible tones which change in frequency and/or pitch based on changes in sand data sensed.

6. Method of treating an undesired physiological condition in a person comprising utilizing biofeedback apparatus according to claim 1 by attaching to the person the sensor unit; exposing said person to said visual or pictorial representations on said image display means corresponding to a physiological condition of the person to be treated; and controlling change in said visual or pictorial representations by said person providing a state of relaxation which affects said at least one psycho-physiological parameter being sensed to thereby cause said visual or pictorial representations to gradually change so that the physiological condition shown in the visual or pictorial representations correspond to a desired physiological condition.

7. Method of treating an undesired physiological condition of a person comprising connecting the person to a biofeedback apparatus, said apparatus including means to sense at least one psycho-physiological parameter of the person and provide a visual or pictorial representations viewable by the person which correspond to a physiological condition to be treated in the person, said visual or pictorial representations gradually changing based on gradual changes sensed in the at least one psycho-physiological parameter;

viewing of said visual or pictorial representations by said person; and controlling change in said visual or pictorial representations by said person providing a state of relaxation which affects the at least one psycho-physiological parameter being sensed to thereby cause said visual or pictorial representations to gradually change so that the physiological condition shown in the visual or pictorial representations correspond to a desired physiological condition.

8. Method of treating an undesired physiological condition in a person comprising utilizing biofeedback apparatus according to claim 2 by attaching to the person the sensor unit; exposing said person to said visual or pictorial representations on said image display means corresponding to a physiological condition of the person to be treated; and controlling change in said visual or pictorial representations by said person providing a state of relaxation which affects said at least one psycho-physiological parameter being sensed to thereby cause said visual or pictorial representations to gradually change so that the physiological condition shown in the visual or pictorial representations correspond to a desired physiological condition.

9. Method of treating an undesired physiological condition in a person comprising utilizing biofeedback apparatus according to claim 3 by attaching to the person the sensor unit; exposing said person to said visual or pictorial representations on said image display means corresponding to a physiological condition of the person to be treated; and controlling change in said visual or pictorial representations by said person providing a state of relaxation which affects said at least one psycho-physiological parameter being sensed to thereby cause said visual or pictorial representations to gradually change so that the physiological condition shown in the visual pictorial representations correspond to a desired physiological condition.

10. Method of treating an undesired physiological condition in a person comprising utilizing biofeedback apparatus according to claim 4 by attaching to the person the sensor unit; exposing said person to said visual or pictorial representations on said image display means corresponding to a physiological condition of the person to be treated; and controlling change in said visual or pictorial representations by said person providing a state of relaxation which affects said at least one psycho-physiological parameter being sensed to thereby cause said visual or pictorial representations to gradually change so that the physiological condition shown in the visual or pictorial representations correspond to a desired physiological condition.

11. Method of treating an undesired physiological condition in a person comprising utilizing biofeedback apparatus according to claim 5 by attaching to the person the sensor unit; exposing said person to said visual or pictorial representations on said image display means corresponding to a physiological condition of the person to be treated; and controlling change in said visual or pictorial representations by said person providing a state of relaxation which affects said at least one psycho-physiological parameter being sensed to thereby cause said visual or pictorial representations to gradually change so that the physiological condition shown in the visual or pictorial representations-correspond to a desired physiological condition.

* * * * *

UNITED STATES PATENT AND TRADEMARK OFFICE
CERTIFICATE OF CORRECTION

PATENT NO. : 6,026,322
DATED : February 15, 2000
INVENTOR(S) : Ernesto Marcelo Dario Korenman et al Page 1 of 1

It is certified that error appears in the above-identified patent and that said Letters Patent is hereby corrected as shown below:

Column 1,
Line 7, "and and" should read -- and --.

Column 4,
Line 29, "described.," should read -- described. --.

Column 10,
Line 18, "coloir" should read -- color --.
Line 37, "comnensate" should read -- compensate --
Line 45, "runnig" should read -- running --.
Line 51, "miake" should read -- make --.

Column 11,
Line 9, insert -- claims. -- following "appended".

On the Title page, the Related U.S. Application Data" is incorrect and should read -- Related U.S. Application Data
[62] Continuation-in-part of application No. 08/754,102, Nov. 20, 1996, which is a continuation of application No. 08/190,163 Feb. 7, 1994, filed as application No. PCT/GB92/01477, Aug. 7, 1992, abandoned. --

Signed and Sealed this

Twenty-first Day of August, 2001

Attest:

*Nicholas P. Godici*

Attesting Officer

NICHOLAS P. GODICI
*Acting Director of the United States Patent and Trademark Office*